US007749521B2

(12) United States Patent
Martens et al.

(10) Patent No.: US 7,749,521 B2
(45) Date of Patent: Jul. 6, 2010

(54) CRYSTALLINE MESOPOROUS OXIDE BASED MATERIALS USEFUL FOR THE FIXATION AND CONTROLLED RELEASE OF DRUGS

(75) Inventors: Johan Adriaan Martens, Huldenberg (BE); Christine Eva Antonia Kirschhock, Darmstadt (DE); Sebastien Philippe Brigitte Kremer, Schaarbeek (BE); Alexander Jan Maria Herman Eugeen Aerts, Schaarbeek (BE); Guy Van Den Mooter, Pellenberg (BE); Jan Van Humbeeck, Haasrode (BE)

(73) Assignee: K.U. Leuven Research & Development, Leuven (BE)

( * ) Notice: Subject to any disclaimer, the term of this patent is extended or adjusted under 35 U.S.C. 154(b) by 529 days.

(21) Appl. No.: 10/562,307

(22) PCT Filed: Jun. 28, 2004

(86) PCT No.: PCT/BE2004/000094

§ 371 (c)(1),
(2), (4) Date: Dec. 23, 2005

(87) PCT Pub. No.: WO2005/000740

PCT Pub. Date: Jan. 6, 2005

(65) Prior Publication Data

US 2006/0134219 A1    Jun. 22, 2006

(30) Foreign Application Priority Data

Jun. 27, 2003    (GB)    ................................. 0315012.5

(51) Int. Cl.
*A61K 9/00* (2006.01)
(52) U.S. Cl. ........................ 424/400; 977/700; 977/712; 977/831
(58) Field of Classification Search ........................ None
See application file for complete search history.

(56) References Cited

U.S. PATENT DOCUMENTS

| 3,639,637 | A | 2/1972 | Campbell |
| 4,235,892 | A | 11/1980 | Nagabhushan |
| 5,057,296 | A | 10/1991 | Beck |
| 5,102,643 | A | 4/1992 | Kresge et al. |
| 5,646,131 | A | 7/1997 | Badwan et al. |
| 6,592,764 | B1 | 7/2003 | Stucky et al. |
| 6,630,170 | B2 | 10/2003 | Balkus, Jr. et al. |
| 6,669,924 | B1 | 12/2003 | Kaliaguine et al. |
| 6,989,254 | B2 | 1/2006 | Wei et al. |
| 2001/0044409 | A1 | 11/2001 | Ghebre-Sellassie et al. |
| 2001/0048946 | A1 | 12/2001 | Ghebre-Sellassie |
| 2004/0106178 | A1 | 6/2004 | Ackerman et al. |

FOREIGN PATENT DOCUMENTS

| EP | 0 403 383 | 12/1990 |
| WO | WO 99/12524 | 3/1999 |
| WO | WO 02/10218 A1 | 2/2002 |
| WO | WO 02/068454 A2 | 9/2002 |

OTHER PUBLICATIONS

Kremer et al. Tiltin Silicalite-1 Nanoslabs into 3D mosaics, Adv. Mater. Oct. 16, 2003.*
Kirschhock et al., Zeosil Nanoslabs: Building Blocks in nPr4N+-mediated Synthesis of MFI Zeolite Angew. Chem. Int. Ed 2001.*
Camblor et al., "Characterization of Nanocrystalline Zeolite Beta," *Microporous and Mesoporous Materials* 25: 59-74 (1998).
Kremer et al., "Tiling Silicalite-1 Nanoslabs into 3D Mosaics," *Advanced Materials* 15(20): 1705-1707 (2003).
Ravishankar et al., "Characterization of Nanosized Material Extracted from Clear Suspensions for MFI Zeolite Synthesis," *J. Phys. Chem. B.* 103(24): 4960-4964 (1999).
Vallet-Regi et al., "A New Property of MCM-41: Drug Delivery System," *Chem. Mater.* 13(2): 308-311 (2001).
Extended European Search Report (EP Application Serial No. EP 07 01 1368), mailed Sep. 26, 2007.
Camblor et al., "Characterization of Nanocrystalline Zeolite Beta," *Microporous and Mesoporous Materials* 25:59-74 (1998).
Kremer et al., "Tiling Silicate-1 Nanoslabs Into 3D Mosaics," *Adv. Mater.* 15:1705-1707 (2003).
Ravishankar et al., "Characterization of Nanosized Material Extracted from Clear Suspensions for MFI Zeolite Synthesis," *J. Phys. Chem. B.* 103:4960-4964 (1999).
International Search Report (PCT/BE2004/000094) (mailed Jan. 7, 2005).
Written Opinion of the International Searching Authority (PCT/BE2004/000094) (mailed Jan. 7, 2005).
Amidon et al., "A Theoretical Basis for a Biopharmaceutic Drug Classification: The Correlation of in Vitro Drug Product Dissolution and in Vivo Bioavailability," *Pharm. Res.* 12:413-420 (1995).
Huo et al., "Mesostructure Design with Gemini Surfactants: Supercage Formation in a Three-Dimensional Hexagonal Array," *Science*, 268:1324-1327 (1995).
Martinez et al., "Applying the Biopharmaceutics Classification System to Veterinary Pharmaceutical Products, Part I: Biopharmaceutics and Formulation Considerations," *Adv. Drug Deliv. Rev.* 54:805-824 (2002).

(Continued)

*Primary Examiner*—Michael G Hartley
(74) *Attorney, Agent, or Firm*—Clark & Elbing LLP

(57) ABSTRACT

The invention describes a new class of crystalline silica material having two levels or porosity and structural order. At the first level, building units are nanoslabs of uniform size having zeolite framework. At the second structural level, nanoslabs are assembled, e.g. linked through their corners, edges or faces following patterns imposed by interaction with cationic surfactant or triblock copolymer molecules. After evacuation of these molecules, microporosity is obtained inside the nanoslabs, and a precise mesoporosity between the nanoslabs depending on the tiling pattern of the zeolite nanoslabs, as evidenced by X-ray diffraction. These materials are useful for the fixation of biologically active species, such as poorly soluble drugs.

12 Claims, 6 Drawing Sheets

OTHER PUBLICATIONS

Voorspoels et al., "Pharmacokinetics of Florfenicol After Treatment of Pigs with Single Oral or Intramuscular Doses or with Medicated Feed for Three Days," *Vet. Rec.* 145:397-399 (1999).

Office Action for Chinese Patent Application No. 200480018101.6, mailed Dec. 8, 2006.

Office Action for European Application No. EP 04 737 677.7, dated Mar. 14, 2007.

Office Action for European Application No. EP 04 737 677.7, dated Feb. 6, 2008.

Office Action for European Application No. EP 07 011 368.3, dated May 14, 2008.

Office Action for European Application No. EP 07 011 368.3, dated Nov. 28, 2008.

Office Action for Australian Patent Application No. 20044251792, dated Jan. 28, 2009.

Office Action for European Patent Application No. EP 07 011 368.3, dated Nov. 24, 2009.

International Preliminary Report on Patentability (PCT/BE2004/000094) (Issued Jan. 3, 2006).

Office Action for European Application No. EP 07 011 368.3 dated Aug. 5, 2009.

Office Action for Israeli Patent Application No. IL 172525, dated Nov. 19, 2009, and an English language translation of the comments and suggestions in the Office Action.

* cited by examiner

CRYSTALLINE MESOPOROUS OXIDE BASED MATERIALS USEFUL FOR THE FIXATION AND CONTROLLED RELEASE OF DRUGS

FIELD OF THE INVENTION

The present invention relates a new class of crystalline silica, said materials having two levels of porosity and structural order and their use for fixation and release of biological and chemical compounds, e.g. drugs.

BACKGROUND OF THE INVENTION

Porous inorganic solids have found great utility as catalysts and separations media for industrial application. The openness of their microstructure allows molecules access to the relatively large surface areas of these materials that enhance their catalytic and sorptive activity. The porous materials in use today can be sorted into three broad categories using the details of their microstructure as a basis for classification. These categories are the amorphous and paracrystalline supports, the crystalline molecular sieves and modified layered materials. The detailed differences in the microstructures of these materials manifest themselves as important differences in the catalytic and sorptive behavior of the materials, as well as in differences in various observable properties used to characterize them, such as their surface area, the sizes of pores and the variability in those sizes, the presence or absence of X-ray diffraction patterns and the details in such patterns, and the appearance of the materials when their microstructure is studied by transmission electron microscopy and electron diffraction methods.

Amorphous and paracrystalline materials represent an important class of porous inorganic solids that have been used for many years in industrial applications. Typical examples of these materials are the amorphous silicas commonly used in catalyst formulations and the paracrystalline transitional aluminas used as solid acid catalysts and petroleum reforming catalyst supports. The term "amorphous" is used herein to indicate a material with no long range order, although almost all materials are crystalline to some degree, at least on the local scale. An alternate term that has been used to described these materials is "X-ray indifferent". The microstructure of silicas consists of 10-25 nm particles of dense amorphous silica, with porosity resulting from voids between the particles. Since there is no long range order in these materials, the pore sizes tend to be distributed over a rather large range. This lack of order also manifests itself in the X-ray diffraction pattern, which is usually featureless.

Paracrystalline materials such as the transitional aluminas also have a wide distribution of pore sizes, but better defined X-ray diffraction patterns usually consisting of a few broad peaks. The microstructure of these materials consists of tiny crystalline regions of condensed alumina phases and the porosity of the materials results from irregular voids between these regions. Since, in the case of either material, there is no long range order controlling the sizes of pores in the material, the variability in pore size is typically quite high. The sizes of pores in these materials fall into a regime called the mesoporous range which is from about 1.3 nm to about 20 nm.

In sharp contrast to these structurally ill-defined solids are materials whose pore size distribution is very narrow because it is controlled by the precisely repeating crystalline nature of the materials, microstructure. These materials are called "molecular sieves", the most important examples of which are zeolites.

Zeolites, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of smaller cavities which may be interconnected by a number of still smaller channels or pores. These cavities and pores are uniform in size within a specific zeolite material. Since the dimensions of these pores are such as to accept for adsorption molecules of certain dimensions while rejecting those of larger dimensions, these materials are known as "molecular sieves" and are utilized in a variety of ways to take advantage of these properties.

Such molecular sieves, both natural and synthetic, include a wide variety of positive ion-containing crystalline silicates. These silicates can be described as a rigid three-dimensional framework of $SiO_4$ and Periodic Table Group IIIB element oxide, e.g. $AlO_4$, in which the tetrahedra are crosslinked by the sharing of oxygen atoms whereby the ratio of the total Group IIIB element, e.g. aluminum, and Group IVB element, e.g. silicon, atoms to oxygen atoms is 1:2.

Generally, porous substances are divided by pore size, for example, pore sizes smaller than 2 nm classified as microporous substances, between 2 and 50 nm classified as mesoporous substances and larger than 50 nm classified as macroporous substances. Of the porous substances, those having uniform channel, such as zeolite, are defined as molecular sieves and up to hundreds of types of species have been found and synthesized thus far. Zeolites play an important role as catalysts or carriers in modern chemical industries by virtue of their characteristics including selective adsorptivity, acidity and ion exchangeability. However, the molecular size of a reactant which can be utilized in catalyst conversion reactions, etc. is limited by the pore size of zeolite because zeolite is a microporous molecular sieve. For example, when ZSM-5 zeolite is applied in a catalytic cracking reaction, its reactivity becomes significantly decreased as the reactant changes from n-alkane to cycloalkane and further to branched alkane. Hence, an enormous effort has been made all over the world to synthesize molecular sieves having larger pores than that of zeolite. As a result, $AlPO_4$, VPI-5, Cloverlite and JDF-20 having larger pore size than that of zeolites were developed. However, these molecular sieves cannot exceed the microporous limit.

Among solid substances known thus far, those having uniform channels, such as zeolites of porous crystalline aluminum silicate and of porous crystalline aluminum phosphates ($AlPO_4$) are defined as molecular sieves, because they selectively adsorb molecules smaller than the size of the channel entrance or they allow molecules to pass through the channel. In view of crystallography, zeolite and $AlPO_4$ are fully crystalline substances, in which atoms and channels are arranged in complete regularity. These fully crystalline molecular sieves are obtained naturally or synthesized through hydrothermal reactions. The number of fully crystalline molecular sieves obtained or synthesized thus far amount to several hundred species. They play an important role as catalysts or supports in modern chemical industries by virtue of their characteristics including selective adsorption, acidity and ion exchangeability. Examples of the current catalyst processes utilizing the characteristics of zeolite include the petroleum cracking reaction using ZSM-5 and the aromatic conversion reaction of paraffin using KL-zeolite impregnated with platinum. A significant problem of the fully crystalline molecular sieve is that it cannot be used in reactions of molecules larger than about 1.3 nm in size.

A series of mesoporous molecular sieves; including MCM-41 and MCM-48, was reported in U.S. Pat. Nos. 5,057,296 and 5,102,643. These molecular sieves show a structure in which mesopores uniform in size are arranged regularly. MCM-41, has a uniform structure exhibiting hexagonal arrangement of straight mesopores, such as honeycomb, and has a specific surface area of about 1,000 m$^2$/g as measured by ordinary BET.

Existing molecular sieves have been produced by using inorganic or organic cations as templates, whereas those mesoporous molecular sieves are synthesized through a liquid crystal template pathway by using surfactants as templates. These mesoporous molecular sieves have the advantage that their pore sizes can be adjusted in a range of 1.6 to 10 nm by controlling the kinds of surfactants or synthetic conditions employed during the production process.

Mesoporous molecular sieves designated as SBA-1, -2 and 3 were reported in Science (1995) 268:1324. Their channels are regularly arranged, while the constituent atoms show an arrangement similar to that of amorphous silica. Mesoporous molecular sieves have regularly arranged channels larger than those of existing zeolites, thus enabling their application to adsorption, isolation or catalyst conversion reactions of relatively large molecules.

U.S. Pat. No. 6,592,764 discloses a family of high quality, hydrothermally stable and ultra large pore size mesoporous silicas by using amphiphilic block copolymers in acidic media. One member of the family, SBA-15, has a highly ordered, two-dimensional hexagonal (p6mm) honeycomb, hexagonal cage or cubic cage mesostructure. Calcination at 500° C. yields porous structures with high BET surface areas of 690 to 1,040 m$^2$/g, and pore volumes up to 2.5 cm$^3$/g, ultra large d(100) spacings of 7.45-45 nm, pore sizes from 4.6-50 nm and silica wall thicknesses of 3.1-6.4 nm. SBA-15 can be readily prepared over a wide range of specific pore sizes and pore wall thicknesses at low temperature (35-80° C.) using a variety of commercially available, non-toxic and biodegradable amphiphilic block copolymers, including triblock polyoxyalkylenes.

U.S. Pat. No. 6,630,170 discloses a mesoporous composition prepared from a mixture comprising hydrochloric acid, vitamin E and a silica source, wherein said vitamin E functions as a templating molecule, and said mesoporous composition exhibits uniform pore size.

U.S. Pat. No. 6,669,924 discloses a mesoporous zeolitic material having a stereoregular arrangement of uniformly-sized mesopores with diameters ranging from 2 to 50 nm and walls having a thickness of at least 4 nm and a microporous nanocrystalline structure, the mesopore walls having a stereoregular arrangement of uniformly-sized micropores with diameters less than 1.5 nm. It also discloses a method of preparing such a mesoporous zeolitic material, comprising the steps of:

a) providing a mesoporous silica having a stereoregular arrangement of uniformly-sized mesopores having diameters ranging from 2 to 50 nm and walls having a thickness of at least 4 nm and an amorphous structure;
b) impregnating said mesoporous silica with a zeolite-templating compound;
c) subjecting the impregnated mesoporous silica obtained in step (b) to a heat treatment at a temperature and for a period of time sufficient to cause transformation of said amorphous structure into a microporous nanocrystalline structure, thereby obtaining a mesoporous zeolitic material with mesopore walls having a stereoregular arrangement of uniformly-sized micropores with diameters less than 1.5 nm; and
d) removing said zeolite-templating compound from the mesoporous zeolitic material obtained in step (c).

The X-ray diffraction patterns of such material as shown in FIGS. 5, 9 and 15 of U.S. Pat. No. 6,669,924 clearly show the presence of several characteristic peaks at angles of diffraction above 3 degrees ($2\theta=6°$). The pore distribution curves of FIG. 14 show that the more conversion is obtained in step (c), the more structural order is lost at the mesoporous level; in practice this means that reproducibility of the material may be impaired by an unaccurate control of the crystallisation time. FIG. 15 also clearly shows that structural order obtained at the mesoporous level in step (a) is lost in steps (b) and (c) when zeolitic structure appears.

Silica molecular sieves with controlled porosity crystallise from hydrogel in the presence of organic template molecules. Patterned, mesoporous silica materials with amorphous walls may be obtained using structure directing surfactants or block copolymers.

The generation of zeolite properties such as acidity and hydrothermal stability in mesostructured materials is a huge research field. The possibility to transform part of the amorphous walls of a mesoporous precursor into zeolite framework was already demonstrated, but segregation of a zeolite phase from the mesostructure as conversion proceeds seems difficult to avoid, as evidenced by U.S. Pat. No. 6,669,924.

There is a need in the art for producing mesoporous oxide based material with high heat stability and improved hydrothermal stability and with improved reproducibility over existing materials.

Another difficult problem for the pharmaceutical industry is the formulation of drugs having low or very low water-solubility into solid dosage forms, especially formulations intended for immediate release. Few solutions to this problem have been disclosed in the art. For instance, U.S. Patent Publication No. 2001/0048946 provides solid dosage forms of sparingly water-soluble pharmaceutical agents, i.e. solid or crystalline drugs having a water-solubility of 10 to 33 µg/ml at 25° C., such as glitazones. More particularly, this document discloses a pharmaceutical composition in the form of a solid particulate dispersion of such a pharmaceutical agent dispersed throughout a matrix of a water-soluble polymer such as polyvinylpyrrolidone, hydroxypropyl cellulose, or hydroxypropyl methylcellulose. In a preferred embodiment, the particulate pharmaceutical agent is dispersed in the water-soluble polymer in a weight ratio of about 10% to about 90% active ingredient to about 90% to about 10% polymer. Other conventional excipients such as glycerin, propyleneglycol, Tween, stearic acid salts and the like can be added.

U.S. Patent Publication No. 2001/0044409 discloses a process for the preparation of a poorly water soluble drug in solid dispersion comprising the steps of (a) blending the drug with a carrier, (b) dissolving a surfactant and a plasticizer/solubilizer in water, (c) spraying the surfactant-plasticizer/solubilizer solution onto the drug/carrier mixture in a fluid bed granulator, (d) extruding the resulting granulation through a twin screw extruder with at least one heating zone, and (e) milling the extrudate to a powdery mass of the solid drug dispersion. Within this process, the carrier may be selected from the group consisting of polyvinylpyrrolidone, high molecular weight polyethylene glycol, urea, citric acid, vinyl acetate copolymer, acrylic polymers, succinic acid, sugars and mixtures thereof; the plasticizer/solubilizer may be selected from the group consisting of low molecular weight polyethylene glycol, propylene glycol, glycerin, triacetin, triethyl citrate, sugar alcohols and mixtures thereof, and the said surfactant may be selected from the group consisting of Tween, Span, Pluronics, polyoxyethylene sorbitol esters, monodiglycerides, polyoxyethylene acid polyoxyethylene alcohol and mixtures thereof. This process suffers from the disadvantage of providing a heating zone in the twin screw extruder and consequently controlling and monitoring the temperature profile of the extruder.

However, none of the above processes appear to be successful in formulating solid dosage forms of drugs having very low water-solubility, i.e. a solubility lower than 10 μg/ml, preferably lower than 5 μg/ml. This problem is applicable to a large number of drugs, including those belonging to the family of diaminopyrimidines, such as stated in U.S. Pat. No. 6,211,185.

U.S. Pat. No. 3,639,637 discloses oestrogen compositions for the preparation of stable aqueous suspensions that can be sprayed onto animal feed, comprising (by weight) 70-95% of water-dispersible gel-forming microcrystalline cellulose and 5-30% of finely-divided diethylstilbestrol (a compound which is virtually insoluble in water) and optionally further up to one third of the weight of the composition of a hydrocolloid selected from the group consisting of sodium carboxy-methylcellulose, methylcellulose and hydroxyethylcellulose. The two latter cellulose compounds are known, namely from EP-A-403,383, to contribute to an extended linear drug release rate.

WO-A-99/12524 solves the problem of drug formulations with both a relatively fast or quick onset of the therapeutic effect and the maintenance of a therapeutically active plasma concentration for a relatively long period of time, by providing an oral modified release multiple-units composition wherein the unit dosage form comprises at least (i) a first fraction being able to release at least 50% of the drug within the first 20 minutes of a certain dissolution method, and (ii) a second fraction for delayed and extended release of the drug. The multiple-units of the first fraction may be granulates or, provided that a surfactant is added to the formulation, coated or uncoated pellets. Formulation of the first fraction depends on the specific drug but typically includes wet-granulation, and an antacid-like or other alkaline substance was found to have a pronounced increasing effect on the release rate.

U.S. Pat. No. 5,646,131 discloses (example 4) rapidly dissolving capsules containing a granulate formulation of a water-insoluble or sparingly soluble drug, such as terfenadine (less than 0.01 mg/ml water-solubility), surfactants (Tween 80 and sodium lauryl sulfate), cyclodextrin, Avicel PH 101 (microcrystalline cellulose) and a disintegrant/swelling agent (Primojel®, i.e. sodium carboxymethyl starch) in a weight ratio of 10:72 to Avicel. These capsules provide better drug absorption, due to the presence of cyclodextrin, as evidenced by the figure showing a 90% drug release within 45 minutes.

U.S. Pat. No. 4,235,892 discloses a series of 1-aryl-2-acylamido-3-fluoro-1-propanol antibacterial agents including D-(threo)-1-p-methylsulfonyl phenyl-2-dichloroacetamido-3-fluoro-1-propanol, an antibacterial agent known as florfenicol and useful for veterinary purposes. Florfenicol has low solubility in water (about 1.3 mg/ml), as well as in many pharmaceutically acceptable organic solvents such as 1,2-propanediol, glycerin, and benzyl alcohol. For oral administration, these 1-aryl-2-acylamido-3-fluoro-1-propanol may be compounded in the form of tablets, or may even be admixed with animal feed. U.S. Pat. No. 4,235,892 therefore discloses making tablets by compressing granules of a composition comprising the said 1-aryl-2-acylamido-3-fluoro-1-propanol (in a drug loading range from 8.3% to 41.7% by weight), lactose, microcrystalline cellulose, starch and magnesium stearate.

The Biopharmaceutical Classification System (hereinafter referred as BCS) according to G. Amidon et al. in *Pharm. Res.* (1995) 12:413-420 provides for two classes of poorly soluble drugs, i.e. Class II and Class IV, and a class of highly soluble drugs, i.e. Class I. According to M. Martinez et al., Applying the Biopharmaceutical Classification System to Veterinary Pharmaceutical Products (Part I: Biopharmaceutics and Formulation Consideration) in *Advanced Drug Delivery Reviews* (2002) 54:805-824, a drug substance should be classified as highly soluble when the highest dose strength is soluble in at most 250 ml of aqueous media over the pH range 1-7.5. In view of its water solubility (1.3 mg/ml) and of a maximal dose of 20 mg/kg for pigs, it is easy to calculate that the highest dose strength of florfenicol administered to pigs is soluble in an amount of water which is well above the limit value for the definition of a class I BCS highly soluble drug. Furthermore it is known from J. Voorspoels et al. in *The Veterinary Record* (October 1999) that florfenicol has a good oral bioavailability, so that it can be classified as a Class II compound as it is not a highly soluble drug and it shows no absorption problems.

There is a specific need in the art to provide a solid formulation of drugs with a water-solubility like florfenicol or lower. Florfenicol is a drug for oral administration to warm-blooded animals, such as cattle with naturally-occurring bovine respiratory disease, swine, sheep, goats and poultry, which at present is only available in the form of injectable solutions. Until now the skilled person has failed in the design of such a solid formulation of florfenicol, which can further be admixed with animal feed if necessary. Also there is a need for a solid formulation for low solubility drugs for human therapies.

Similar problems, yet unsolved in a suitable manner, arise with a growing number of therapeutic drugs with poor solubility like for instance itraconazole and diazepam. Solving such problems constitutes another goal of the present invention.

SUMMARY OF THE INVENTION

The present invention is based on the unexpected finding that both problems of improving the reproducibility of mesoporous oxide based materials and/or of formulating poorly soluble drugs, especially for immediate release, can be solved at the same time by providing a substantially crystalline mesoporous oxide based material, e.g. a silica material, being obtained by assembly of nanometer size building units having zeolite framework, wherein said assembly proceeds in the presence of one or more amphiphilic non-anionic surfactants, wherein said substantially crystalline mesoporous oxide based material has two or more levels of porosity and structural order, and wherein the internal structure of said nanometer size building units do not give rise to Bragg type diffraction in a powder X-ray diffraction pattern of said substantially crystalline mesoporous oxide based material. Such a novel material may easily be produced in a two-step procedure and is able to entrap a biologically active species of a suitable size, especially a poorly soluble drug with a molecular weight in the range of about 200 to 1,000 (daltons), and provide immediate release of said drug when formulated into a pharmaceutical preparation. The invention also relates to the use of amphiphilic non-anionic molecules, such as cationic surfactants and poly(alkylene oxide) triblock copolymers, for the assembly of nanometer size building units having zeolite framework.

DETAILED DESCRIPTION OF THE DRAWINGS

FIG. 1 shows in the upper part (a) the X-ray diffraction pattern, at interplanar spacings from 1.0 to 5.0 nm (with an enlarged insert for interplanar spacings from 1.0 to 3.0 nm) and in the lower part (b) a high resolution electron microscopy (hereinafter HREM) image (with a first insert for a scale bar representing 10 nm at bottom left, and a second insert for the Fourier transform at top right) of a mesoporous silica material according to an embodiment of the invention named Zeotile-1. The X-ray diffraction pattern is indexed according to the hexagonal tiling of nanoslabs (2.6×2.0×4.0 nm$^3$) as shown on the HREM image.

DETAILED DESCRIPTION OF THE INVENTION

Figure 1:
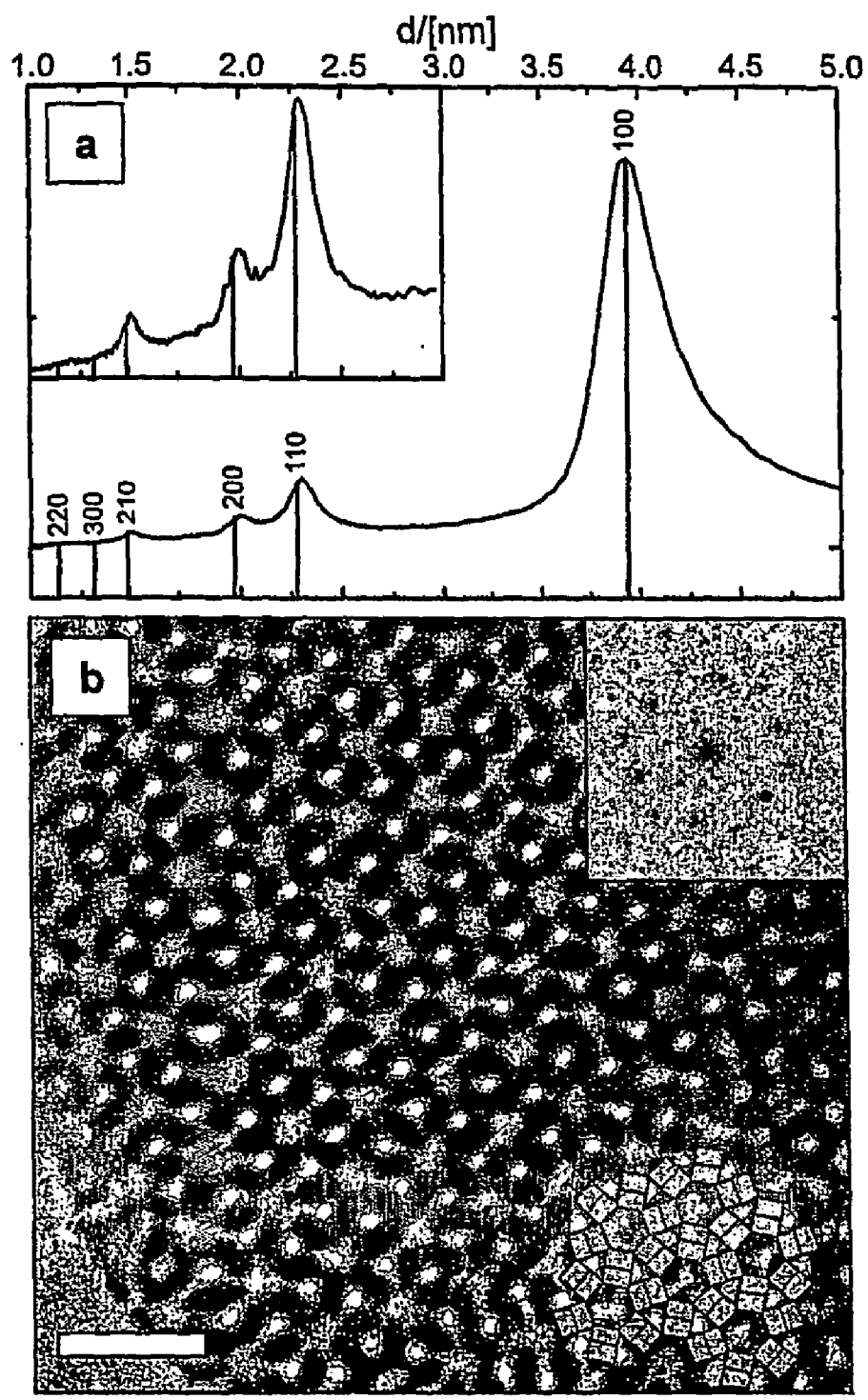

In a first aspect, the present invention describe a new class of crystalline oxide materials, especially silica materials, said materials having two levels of porosity and structural order. At the first level, building units are nanoslabs of substantially uniform size having a zeolite framework (e.g. Silicalite-1) generated e.g. by the tetrapropylammonium template. At the second structural level, nanoslabs are linked through their corners, edges or faces following patterns imposed by interaction with cationic surfactant or triblock copolymer molecules. Without being limited by theory it is believed that after evacuation of the organic molecules, microporosity is obtained inside the nanoslabs, and a precise mesoporosity between the nanoslabs depending on the tiling pattern of the zeolite slabs. Therefore, the use of cationic surfactants (preferably quaternary ammonium salts) or triblock copolymer molecules in order to impose an organisation to the nanoslabs is a second object of the invention. In a first embodiment four different tiling patterns were prepared and directly imaged by electron microscopy. X-ray diffraction confirms the mosaic structures derived from electron microscopy. Application fields are catalysis and molecular separation, adsorption of metal ions, fixation of biologically active species, electro-optical and dielectric materials.

In this first aspect, the invention relates to a crystalline mesoporous silica material being obtained by assembly of nanometer size building units having zeolite framework, said crystalline mesoporous silica material having two or more levels of porosity and structural order, and wherein the internal structure of said nanometer size building units does not give rise to Bragg type diffraction in a powder X-ray diffraction pattern of said crystalline mesoporous silica material. For example, said building units may be nanoslabs of substantially uniform size having a Silicalite-1 zeolite framework. Such nanoslabs may be generated by tetrapropylammonium-ion mediation, for instance as disclosed by Kirschhock et al. in *Angew. Chem. Int. Ed.* (2001) 40:2637-2640. In this crystalline mesoporous silica material, said two or more levels of porosity usually comprise microporosity and mesoporosity, e.g. at least a microporosity inside said nanoslabs and at least a mesoporosity between said nanoslabs. Said nanoslabs are preferably linked through their corners, edges or faces following patterns imposed by interaction with a cationic surfactant or triblock copolymer molecule. An exemplary cationic surfactant is cetyltrimethyl-ammonium bromide, and an exemplary triblock copolymer is a Pluronic P123 triblock copolymer $EO_{20}PO_{70}EO_{20}$ (wherein EO stands for ethylene oxide, and PO stands for propylene oxide).

In a crystalline mesoporous silica material according to this first aspect of the invention, nanoslabs may for instance be forced into face-sharing double units with a size ranging from about 2 to 4 nm and linked in a hexagonal symmetry pattern. The crystalline mesoporous silica material according to the invention may be obtained from nanoslabs with a size ranging from about 1.3 to 8.0 nm, and/or from stapled nanoslabs arranged in a hexagonal appearing tile.

The crystalline mesoporous silica materials according to this first aspect of the invention are useful in a number of industrial applications, such as, but not limited to, the fixation of biologically active species, as well as an electro-optical or dielectric material or for catalysis, molecular separation or adsorption of metal ions.

Thus the invention also relates to a novel use of a cationic surfactant or a triblock copolymer molecule for the assembly of nanoslabs of substantially uniform size having the Silicalite-1 zeolite framework, for instance wherein said assembly proceeds while imparting a structural organisation to said nanoslabs. This is especially useful when said nanoslabs become linked through their corners, edges or faces following patterns imposed by interaction with said cationic surfactant or triblock copolymer molecule. Said cationic surfactant may be cetyltrimethylammonium bromide, and said triblock copolymer may be a Pluronic P123 triblock copolymer $EO_{20}PO_{70}EO_{20}$ (with the meaning indicated above).

The invention also relates to a process for making a novel crystalline mesoporous oxide material, especially a silica material, such as above defined, comprising the steps of (a) generating nanoslabs having zeolite framework by tetrapropylammonium-ion mediation and (b) assembling said nanoslabs through interaction with a cationic surfactant or triblock copolymer molecule. Said cationic surfactant may be cetyltrimethylammonium bromide, and said triblock copolymer may be a Pluronic P123 triblock copolymer $EO_{20}\ PO_{70}EO_{20}$ (with the meaning indicated above). This process optionally further comprises the step, of removing said tetrapropylammonium-ion and said cationic surfactant or triblock copolymer molecule, wherein said removal may be effected for instance through oxidation (e.g. by means of a strong acid such as nitric acid) and/or solvent leaching (e.g. using ethanol) and/or calcination.

The crystalline mesoporous oxide material, e.g. silica material, according to this first aspect of the invention is easily distinguishable from other mesoporous materials. The absence of Bragg type diffraction from the internal structure of nanometer size building units clearly manifests itself by the absence of peaks in a powder X-ray diffraction pattern at interplanar spacings below about 1.5 nm, as shown for instance in FIG. 1-*a*. All characteristic peaks of said X-ray diffraction pattern being located at interplanar spacings above about 1.5 nm are related to the tiling pattern of the nanoslabs, not their internal structure. Preferably for such characterisation, the powder X-ray diffraction pattern should be performed after removal of the tetrapropylammonium-ion and cationic surfactant or triblock copolymer molecule, in order to avoid any interfering peaks from such molecules.

In a similar but much broader concept, the invention relates to a substantially crystalline mesoporous oxide based material being obtained by assembly of nanometer size building units having zeolite framework, wherein said assembly proceeds in the presence of one or more amphiphilic non-anionic surfactants, wherein said substantially crystalline mesoporous oxide based material has two or more levels of porosity and structural order, and wherein the internal structure of said nanometer size building units does not give rise to Bragg type diffraction in a powder X-ray diffraction pattern of said substantially crystalline mesoporous oxide based material. Such a material is easily distinguishable from other mesoporous materials known in the art, using analytical techniques well known to the skilled person. The absence of Bragg type diffraction from the internal structure of nanometer size building units manifests itself by the absence of peaks in a powder X-ray diffraction pattern at interplanar spacings below about 1.5 nm and/or at angles of diffraction Θ above about 3 degrees (2Θ above about 6 degrees). Preferably, said powder X-ray diffraction pattern should be performed after removal of said one or more amphiphilic non-anionic surfactants, in order to avoid any interfering peaks from such molecules.

In the substantially crystalline mesoporous oxide based material according to the invention, said oxide based material may comprise one or more oxides selected from the group consisting of silica, germanium oxide and metallic oxides. A preferred non metallic oxide is silica. The metallic oxides may derive from any metal selected from groups 4 to 12 of the periodic table. Preferred metals are aluminum and transition metals Exemplary metallic oxides are preferably selected from the group consisting of alumina, titania, zirconia, ceria, manganese oxide, niobium oxide, tantalum oxide, tungsten oxide, tin oxide, gallium oxide, iron oxide, and hafnium oxide. The mesoporous oxide based material according to the invention may comprise silica in combination with one or more such metallic oxides which will be selected according to the intended end use of the material. For instance silica, alumina, titania, zirconia and their mixtures in a wide range of proportions may be considered for use as acidic catalysts. A mesoporous tungsten oxide material may be used as a carrier for a number of ruthenium based catalysts for diverse chemical reactions including polymerisation, metathesis, epoxidation, hydro-amination, aziridination and the like. A mesoporous semiconducting oxide material may be used for industrial applications such as the construction of fuel cells.

In view of the fields of application envisaged and the most common industrial requirements, it is preferred that:
  the size of the building units in the material according to the invention ranges from about 1 to 8 nm, and/or
  the oxide based material has one or more types of mesopores each with an average size ranging from about 2 to 15 nm. The term "type of mesopore" as used herein refers to the geometrical shape which is not particularly limited and may be for instance hexagonal, cubic, lamellar and the like, and/or
  said one or more types of mesopores each have a narrow pore size distribution, i.e. a nearly uniform pore size distribution, as may be evidenced for instance from calculation by the Barrett-Joyner-Halenda (hereinafter referred as BJH) analysis from a nitrogen adsorption/desorption isotherm of said mesoporous oxide based material. BJH analysis is commonly used by the skilled person in this field of technology for performing an estimation of size distribution.

According to one embodiment, nanometer size building units present in the oxide based material of the invention may be referred to as nanoslabs (according to the terminology used by Kirschhock et al. in *J. Phys. Chem.* (1999) 103: 11021-11027) of preferably substantially uniform size having a zeolite framework such as, but not limited to, the Silicalite-1 zeolite framework.

According to this invention, nanometer size building units are preferably generated by means of a mediating agent selected from the group consisting of tetraalkylammonium ions, tetraalkylphosphonium ions and gemini (dimeric) tetraalkylammonium ions wherein each alkyl group independently has from 2 to 4 carbon atoms. More preferably, one or more of said alkyl groups is propyl. The term "gemini" as used throughout this specification, in particular with respect to surfactants, refers to an organic molecule consisting of two preferably identical hydrocarbon molecules chemically bonded together by a spacer. The two terminal hydrocarbon tails can be short or long; the two polar head groups can be cationic or non-ionic; the spacer can be short or long. More detailed reference to such compounds may be found in B. S. Sekhon, *Resonance* (March 2004) pp. 4245.

According one embodiment of this invention, nanometer size building units may be linked through their corners, edges or faces following patterns imposed by interaction of said nanometer size building units with said one or more amphiphilic non-anionic surfactants. Said one or more amphiphilic non-anionic surfactants are preferably selected from the group consisting of amphiphilic non-ionic molecules and amphiphilic cationic molecules or substances. For instance the amphiphilic non-anionic substance may be selected from the group consisting of amphiphilic block copolymers, cationic gemini (dimeric) surfactants and $C_{12-18}$ alkyltrimethyl-ammonium halide surfactants. Any halide may be suitable, preferably bromides and chlorides. When an amphiphilic cationic substance is used, e.g. a halide surfactant or a cationic gemini (dimeric) surfactant, it is important for the efficiency of production that the length of the hydrocarbon tail be from about 12 to 18 carbon atoms, preferably from 14 to 16 carbon atoms. Preferred surfactants are hexadecyltrimethylammonium chloride (HTACl), dodecyltrimethyl-ammonium bromide (DTABr), tetradecyltrimethyl ammonium bromide (TTABr) and octadecyltrimethylammonium bromide (OTABr). Under such circumstances, it is also important that interaction proceeds under basic conditions and, in a still more specific embodiment, interaction may proceed in the presence of one or more salts selected from the group consisting of aluminates, borates and acid salts of 3 d transition metals on the periodic table. The preferred organic or inorganic salts, which are able to bind to monovalent cations, such as $Na^+$, $K^+$ and $NH_4^+$, and dissolve in water, are NaCl, KCl, $CH_3COONa$, NaBr, $Na_2SO_4$, $NaNO_3$, $NaClO_4$, $NaClO_3$, ethylenediaminetetracetic acid tetrasodium salt, adipic acid disodium salt, 1,3-benzenedisulfonic acid disodium salt or nitrilotriacetic acid sodium salt. Such water-soluble organic or inorganic salts capable of forming a bond with a monovalent cation are preferably used in amounts from about 1 to 15 moles salt per mole of the alkyltrimethylammonium halide.

When the one or more amphiphilic non-anionic substances is an amphiphilic block copolymer, it is preferred that interaction proceeds under acidic conditions. Suitable amphiphilic non-anionic substances are poly(ethylene, oxide)-poly(alkylene oxide)-poly(ethylene oxide) triblock copoly-mers wherein the alkylene oxide moiety has at least 3 carbon atoms, for instance a propylene oxide or butylene oxide moiety, more preferably such triblock copolymers wherein the number of ethylene oxide moieties in each block is at least 5 and/or wherein the number of alkylene oxide moieties in the central block is at least 30. Alternative suitable surfactants include any non-ionic surfactants with a hydrophilic-lipophilic balance (HLB) from 8 to 30 such as, but not limited to, reaction products of an alkylene oxide, typically ethylene oxide, with a fatty alcohol, a fatty acid, an alkylphenol (e.g. octylphenol or nonylphenol), an alkylamine or similar compounds having at least one active hydrogen atom. Preferably the carbon chain length of such compounds should be from 8 to 18 carbon atoms. Commercially available examples thereof are known under the trade names Mirj 52, Mirj 45 (polyoxyethelene stearate), Pluronic 123 and the like.

A preferred characteristic feature of the substantially crystalline mesoporous oxide based material of the invention is in having two or more levels of porosity comprising at least a microporosity and a mesoporosity, e.g. a microporosity inside said nanometer size building units and at least a mesoporosity between said nanometer size building units. For instance said building units may be assembled or arranged in a hexagonal pattern and may have a size ranging from about 1 to 8 nm. Another feature may consist of having mesopore walls with a thickness from about 1 to 4 nm.

The substantially crystalline mesoporous oxide based material according to the invention has a number of industrial applications such as for water treatment, catalyst support and the like, and is most useful for the fixation or immobilisation of a biologically active species, preferably wherein the molecular weight of said biologically active species is between about 200 and 1,000. Although the active species to be immobilized should in principle any kind of synthetic drug or molecule (including pesticides, insecticides, fungicides and the like), the invention is mainly useful in situations where the characteristics of the drug are such that formulation problems are difficult to solve due to poor water-solubility. Thus, said biologically active species is preferably a poorly soluble therapeutic drug such as one classifiable as belonging to Class II or Class IV of the Biopharmaceutical Classification System and preferably has a water-solubility below about 2.5 mg/ml, even between 0.1 and 1 mg/ml (i.e. "very slightly soluble" as defined in the United States Pharmacopeia), even below 0.1 mg/ml (i.e. "practically insoluble" as defined in the United States Pharmacopeia), even below about 5 µg/ml and may even have a water-solubility as low as about 0.2 µg/ml, at room temperature and physiological pH. Non-limiting examples of such drugs include for instance chlorothiazide, hydrochlorothiazide, nimodipine, flufenamic acid, furosemide, mefenamic acid, bendroflumethiazide, benzthiazide, ethacrinic acid, nitrendipine, itraconazole, saperconazole, troglitazone, prazosin, atovaquone, danazol, glibenciamide, griseofulvin, ketoconazole, carbamazepine, sulfadiazine, florfenicol, acetohexamide, ajamaline, benzbromarone, benzyl benzoate, betamethasone, chloramphenicol, chlorpropamide, chlorthalidone, clofibrate, diazepam, dicumarol, digitoxin, ethotoin, glutethimide, hydrocortisone, hydroflumethiazide, hydroquinine, indomethacin, ibuprofen, ketoprofen, naproxen, khellin, nitrazepam, nitrofurantoin, novalgin, oxazepam, papaverine, phenylbutazone, phenytoin, prednisolone, prednisone, reserpine, spironolactone, sulfabenzamide, sultadimethoxine, sulfamerazine, sulfamethazine, sulfamethoxypyridazine, succinylsulfathiazole, sulfamethizole, sulfamethoxazole (also in admixture with trimethoprim), sulfaphenazole, sulfathiazole, sulfisoxazole, sulpiride, testosterone and diaminopyrimidines. Suitable examples of diaminopyrimidines include, without limitation, 2,4-diamino-5-(3, 4,5-trimethoxybenzyl)pyrimidine (known as trimethoprim), 2,4-diamino-5-(3,4-dimethoxybenzyl)pyrimidine (known as diaveridine), 2,4 diamino-5-(3,4,6-trimethoxybenzyl)pyrimidine, 2,4-diamino-5-(2-methyl-4,5-dimethoxybenzyl)pyrimidine (known as ormetoprim), 2,4-diamino-5-(3,4-dimethoxy-5-bromobenzyl)pyrimidine, and 2,4-diamino-5-(4-chloro-phenyl)-6-ethylpyrimidine (known as pyrimethamine). The above-mentioned drugs are known as belonging to Class II (poorly soluble, highly permeable) or Class IV (poorly soluble, poorly permeable) of the Biopharmaceutical Classification System according to G. Amidon et al. in *Pharm. Res.* (1995) 12:413-420. As will be appreciated by those skilled in the art, these drugs belong to various therapeutic classes, including diuretics, anti-hypertensive agents, anti-viral agents, antibacterial agents, antifungals, etc, and are not limited to human or veterinary use alone. Preferably the size of said biologically active species should be suitable for entrapment into the mesopores of the substantially ordered mesoporous oxide based material of this invention.

This invention also relates to the use of an amphiphilic non-anionic molecule for the assembly of nanometer size building units having zeolite framework, e.g. wherein said assembly proceeds while imparting a structural organisation to said nanometer size building units. Within said the framework of such use, nanometer size building units may be linked through their corners, edges or faces following patterns imposed by interaction with said amphiphilic non-anionic molecule. Suitable amphiphilic non-anionic molecules are as already disclosed hereinabove in details. The nanometer size building units to be assembled typically comprise one or more oxides selected from the group consisting of silica, germanium oxide and metallic oxides, all as previously described herein-above, and the said assembly results in forming a substantially crystalline mesoporous oxide based material preferably having characteristic features such as above stated (in particular with respect to their powder X-ray diffraction pattern).

This invention also provides a process for making a substantially crystalline mesoporous oxide based material such as described herein, said process comprising the steps of (a) generating nanometer size building units having zeolite framework by means of a mediating agent selected from the group consisting of tetraalkylammonium ions, tetraalkylphosphonium ions and gemini (dimeric) tetraalkylammonium ions wherein the alkyl group has from 2 to 4 carbon atoms, and (b) assembling said nanometer size building units through interaction with one or more amphiphilic non-anionic substances to yield a mesoporous oxide based material. Said amphiphilic non-anionic substances are preferably selected from the group consisting of amphiphilic non-ionic molecules and amphiphilic cationic molecules, more preferably selected from the group consisting of amphiphilic block copolymers, cationic gemini (dimeric) surfactants and $C_{12-18}$ alkyltrimethyl-ammonium halide surfactants. In a particular embodiment of the process, the amphiphilic non-anionic substance may be a $C_{12-18}$ alkyltrimethylammonium halide surfactant or a cationic gemini (dimeric) surfactant, wherein interaction proceeds under basic conditions, optionally in the presence of one or more salts selected from the group consisting of aluminates, borates and acid salts of 3d transition metals on the periodic table. In another particular embodiment of the process, the amphiphilic non-anionic substance is a surfactant with a HLB from 8 to 30 and may be an amphiphilic block copolymer, wherein interaction proceeds under acidic conditions. Such amphiphilic block copolymer may be a poly(ethylene oxide)-poly(alkylene oxide)-poly(ethylene oxide) triblock copolymer wherein the alkylene oxide moiety has at least 3 carbon atoms.

Preferably the process of the invention further includes one or more steps such as calcination, oxidation or solvent extraction of the mesoporous oxide based material from step (b) for substantially removing the organic species introduced in steps (a) and (b). This additional step is especially useful when the mesoporous material is intended for applications where said organic species may be regarded as toxic or harmful for the human or animal body, i.e. especially for veterinary or pharmaceutical or agricultural uses.

It is noteworthy that for the fixation or immobilisation of a biologically active species, not only the mesoporous materials described in details herein but also a few alternative mesoporous ordered oxide based materials hating one or more levels of porosity and structural order, provided that when said ordered oxide based material has a single level of porosity and structural order it is obtained in the absence of an alpha-tocopherol polyethylene glycol ester templating biomolecule. Suitable examples of single order oxide based materials include for instance materials named SBA-15 such as disclosed in U.S. Pat. No. 6,592,764, as well as materials disclosed in U.S. Pat. No. 6,669,924. Although such materials are different from and less industrially reproducible than the materials of this invention, they may provide nearly similar advantages in the formulation of biologically active species, preferably poorly soluble therapeutic synthetic drugs (e.g. such drugs classifiable as belonging to Class II or Class IV of the Biopharmaceutical Classification System), provided that the size of said biologically active species is suitable for entrapment into the mesopores of said substantially ordered mesoporous oxide based material (e.g. the molecular weight of said biologically active species is preferably between about 200 and 1,000). Exemplary biologically active species include itraconazole and diazepam.

As explained herein-above, the substantially ordered mesoporous oxide based material preferably has two or more levels of porosity and structural order being preferably obtained by assembly of nanometer size building units having zeolite framework and wherein said assembly proceeds in the presence of one or more amphiphilic non-anionic surfactants. More preferably the internal structure of said nanometer size building units does not give rise to Bragg type diffraction in a powder X-ray diffraction pattern of said substantially crystalline mesoporous oxide based material, as evidenced by the absence of peaks in a powder X-ray diffraction pattern at interplanar spacings below about 1.5 nm and/or at angles of diffraction Θ above 3 degrees (2Θ above 6 degrees), preferably after removal of said one or more amphiphilic non-anionic surfactants.

The above useful invention may take the form of a pharmaceutical composition comprising a biologically active species and a substantially ordered mesoporous oxide based material, wherein said ordered oxide based material has one or more levels of porosity or structural order, provided that when said ordered oxide based material has a single level of porosity and structural order it is obtained in the absence of an alpha-tocopherol polyethylene glycol ester templating biomolecule. Preferably it is a pharmaceutical composition wherein the molecular weight of said biologically active species (preferably a poorly-soluble drug) is between about 200 and 1,000. This pharmaceutical composition may further comprise one or more pharmaceutically acceptable excipients (as is standard in the art), and are especially suitable for providing immediate in vivo release of said biologically active species.

The immediate release pharmaceutical compositions of this invention may further comprise one or more pharmaceutically acceptable fillers. The aforesaid pharmaceutically acceptable fillers may be selected for instance from hydrocolloids (such as xanthan gum), binding agents, glidants, lubricants, surfactants and diluents. The term "pharmaceutically acceptable filler" as used herein is intended to refer to any material which is inert in the sense that it does not have any therapeutic and/or prophylactic effect per se but does not adversely interfere with the therapeutic or prophylactic property of the drug or pharmaceutical active ingredient being formulated. The nature and amount of such fillers are not critical to the present invention. They include for instance binding agents such as starch, gelatin, glucose, alginic acid, sodium and calcium alginates, water-soluble acrylic (co)polymers, polyvinylpyrrolidone, polyaminoacids, ethylene-vinyl acetate copolymers and the like; natural and synthetic mineral fillers or glidants such as fumed (colloidal) silica (e.g. commercially available under the tradename Aerosil®), magnesium silicates such as talc, diatomaceous earth, aluminium silicate such as kaolinite, montmorillonite or mica, magnesium aluminium silicate such as attapulgite and vermiculite, carbon such as charcoal, sulphur and highly dispersed silicic acid polymers; water-soluble diluents such as lactose, sorbitol and the like.

Other excipients of the immediate release pharmaceutical composition of this invention may suitably be selected from the group consisting of poly-ethyleneglycols and polypropyleneglycols having weight number molecular weights between about 300 and about 5,000; glycerol; propyleneglycol and glycerides (such as mono-, di- and triglycerides of polyethyleneglycol fatty acid esters, including those commercially available under the tradename Gelucire®). Suitable examples of the latter include those having both a portion derived from a glyceride and a portion derived from a polyethylene glycol ester. For instance, it is suitable to use polyglycosylated glycerides. The term "polyglycosylated glycerides" as used herein denotes a mixture of mono-, di- and triglycerides with polyethylene glycol (PEG) mono- and diesters of $C_8$-$C_{18}$ fatty acids with a molecular weight preferably between about 200 and about 600, optionally further including glycerol and/or free PEG, the hydrophilic-lipophilic balance (HLB) value of which is controlled by the chain length of the PEG and the melting point of which is controlled by the chain length of the fatty acids, of the PEG and of the degrees of saturation of the fatty chains, and thus of the starting oil. Similarly the expression "$C_8$-$C_{18}$ fatty acids" as used herein denotes mixtures in various proportions of caprylic acid, capric acid, lauric acid, myristic acid, palmitic acid and stearic acid, when these acids are saturated, and the corresponding unsaturated acids. As is well known to the skilled person, the proportions of these fatty acids may vary as a function of the starting oils. Examples of the latter include, but are not limited to, saturated polyglycolized $C_8$-$C_{10}$ glycerides, such as the PEG-8 caprylate/caprate glyceride esters sold by Gattefosse Corporation under the tradename Labrasol; PEG-6 caprylic/capric glycerides sold by Huls Aktiengesellschaft under the trade name Softigen 767; PEG-60 corn glycerides sold by Croda under the trade name Crovol M-70; Ceteareth-20 sold by Henkel Corporation under the trade name Emulgin B2; diethyleneglycol monoethyl-ethers sold by Gattefosse Corporation under the trade name Transcutol; a mixture of $C_8$-$C_{18}$ saturated polyglycosylated glycerides having a melting point within a range of about 42-48° C. and a HLB within a range of about 8 to 16 such as sold by Gattefosse Corporation under the trade names Gelucire 48/09, Gelucire 44/14 and Gelucire 42/12; and mixtures thereof in various proportions. When a polyethyleneglycol is used for instance, it may comprise a higher molecular weight solid fraction and a lower molecular weight liquid fraction, the latter acting as a plasticizer.

In one embodiment of the invention, the biologically active species may be present in the immediate release composition in an amount from about 0.5% to about 50% by weight, preferably from 2 to 40 weight %, more preferably from 5 to 30 weight %, of the composition. As will be easily understood by the skilled person, immediate or fast release is a feature which may significantly vary from drug to drug and from one drug loading to another. For the purpose of the present invention, immediate release means a release of at least 60% of the drug under physiological conditions (pH, temperature) within at most 30 minutes, preferably at most 15 minutes, more preferably at most 10 minutes, for drug loadings within a range from about 5% to 40%, preferably from 10% to 30% by weight, of the pharmaceutical composition.

According to this invention, the immediate release pharmaceutical composition may optionally further comprise one or more other drugs different from the drug having poor water-solubility, but preferably belonging to the same therapeutic class, in particular when combined drug therapy is desired.

As a summary, according to our invention, fast release of poorly soluble drugs can be achieved by loading the drug molecules on a silica carrier material with specific porosity and structural order. There exists an optimum pore diameter range of silica materials in order to achieve this fast release. The optimum pore size is in the range of about 4 to 14 nm, more preferably between 5 and 12 nm, most preferably from about 6 to 10 nm. Preferred are silica carriers with a mean pore diameter within this range, and having a narrow pore size distribution.

The appropriateness of a silica material for the fast drug release application can be evaluated based on the nitrogen adsorption isotherm at −196° C. Appropriate silica materials exhibit type H1 hysteresis loops, following the classification of the international Union for Pure and Applied Chemistry (IUPAC) (Sing et al. in *Pure Appl. Chem.* (1985) 57(4):603, which are characteristic of adsorbents with a narrow distribution of uniform, open ended tubular pores. Silica materials giving rise to hysteresis loops of type H2 or an ill-defined hysteresis loop should be considered as inappropriate for fast drug release.

The mesoporous materials ("zeotiles") of this invention are unexpectedly robust materials combining the advantages of micro- and mesoporous silicate structures. They are able to withstand temperatures up to about 400° C. for several hours in air. The following examples illustrate the structural diversity of the material and its usefulness in drug delivery, in particular for immediate release of poorly soluble drugs. From a structural point of view, other combinations are equally possible and may be produced while using the teachings of the present specification. At the first structural level, nanoslabs or building units with alternative framework types can be used, and heteroatoms can be incorporated. At the second structural level, the tiling pattern can be altered by changing the nature of the structure-providing agent and/or synthesis conditions such as concentration of nanoslabs, composition of nanoslabs, concentration of structure-providing agent, temperature and the like, without departing from the scope of the invention.

Example 1

Nanoslabs were prepared through hydrolysis of tetraethyl ortho-silicate (37.32 g, commercially available from Acros, 98% purity) in 32.13 g of an aqueous tetrapropylammonium hydroxide solution (40% by weight concentration) under stirring. After hydrolysis, 30.55 g water was added and stirring Continued for 24 hours. Nanoslab size (dimensions of 1.3× 2.0×4.0 nm$^3$ in this embodiment) is controlled by synthesis conditions.

Then 60 g of a 10% by weight aqueous solution of cetyltrimethylammonium bromide (commercially available from Acros, 99% purity) heated at 80° C. was combined with 20 g of the nanoslab suspension under continuous stirring for 20 minutes. The precipitate was then recovered by filtration, washed with water and dried at 60° C. for 2 days. The organic templating organic molecules (tetrapropylammonium hydroxide and cetyltrimethylammonium bromide) were removed by slurrying 3 g of the resulting solid in 200 mL ethanol containing 0.02 mole nitric acid at 77° C. for 1 hour. The solid was recovered by filtration and washed with ethanol. Oxidation with nitric acid was repeated twice. The sample was finally dried at 60° C. overnight.

Powder X-ray diffraction (XRD) and high-resolution electron microscopy (HREM), shown in FIG. 1, were used to characterise the obtained superstructures, i.e. the structural order of the material obtained. As shown in FIG. 1-*a*, the XRD spectrum did not reveal internal nanoslab information but only information related to the tiling pattern of said nanoslabs, all characteristic peaks being located at interplanar spacings between 1.5 and 4.0 nm. Individual dispersed nanoslabs, presumably because of their small size, did not give rise to Bragg type diffraction related to their internal structure. In this material, slight misalignments in the tiling prevent the manifestation of this Bragg scattering.

In HREM, a low intensity electron beam and medium magnifications were used to minimise electron beam damage of the structure. The HREM image (FIG. 1-*b*) was taken in overfocus conditions where the image directly represents the structure; the bright dots correspond to the projection of the channels. On this HREM image the schematic projected mosaic structure is superimposed. A first superstructure, herein referred to as Zeotile-1, is present in this sample. In Zeotile-1, nanoslabs are forced into face sharing, double nanoslab units, measuring 2.6×2.0×4.0 nm$^3$ and linked in a hexagonal symmetry pattern. The Fourier transform of the HREM image (insert at top right of the figure) only shows information on the nanoslab tiling; no reflections related to the internal nanoslab structure were detected.

Example 2

10 g of a Pluronic P123 triblock copolymer (commercially available from BASF, formula $EO_{20}PO_{70}EO_{20}$) was dissolved in 90 g water under stirring. 24 g of this solution was combined with 8 g of a 5 M HCl aqueous solution. 18 g of a nanoslab suspension prepared under similar conditions as in the first step of example 1 but with dimensions of 1.3×8.0×4.0 nm$^3$ (obtained through acidification of nanoslab suspension) was slowly combined with another 9 g 5 M HCl solution under vigorous stirring and finally combined with the acidic triblock copolymer solution. The mixture was heated at 90° C. under quiescent conditions during 4 days. A solid product was formed and separated from the liquid by centrifugation at 12,000 rpm. The product was washed with water until pH exceeds 3. The sample was dried at 60° C., and finally calcined at 350° C. with a temperature with a temperature increase of 0.5° C./minute.

Figure 3:
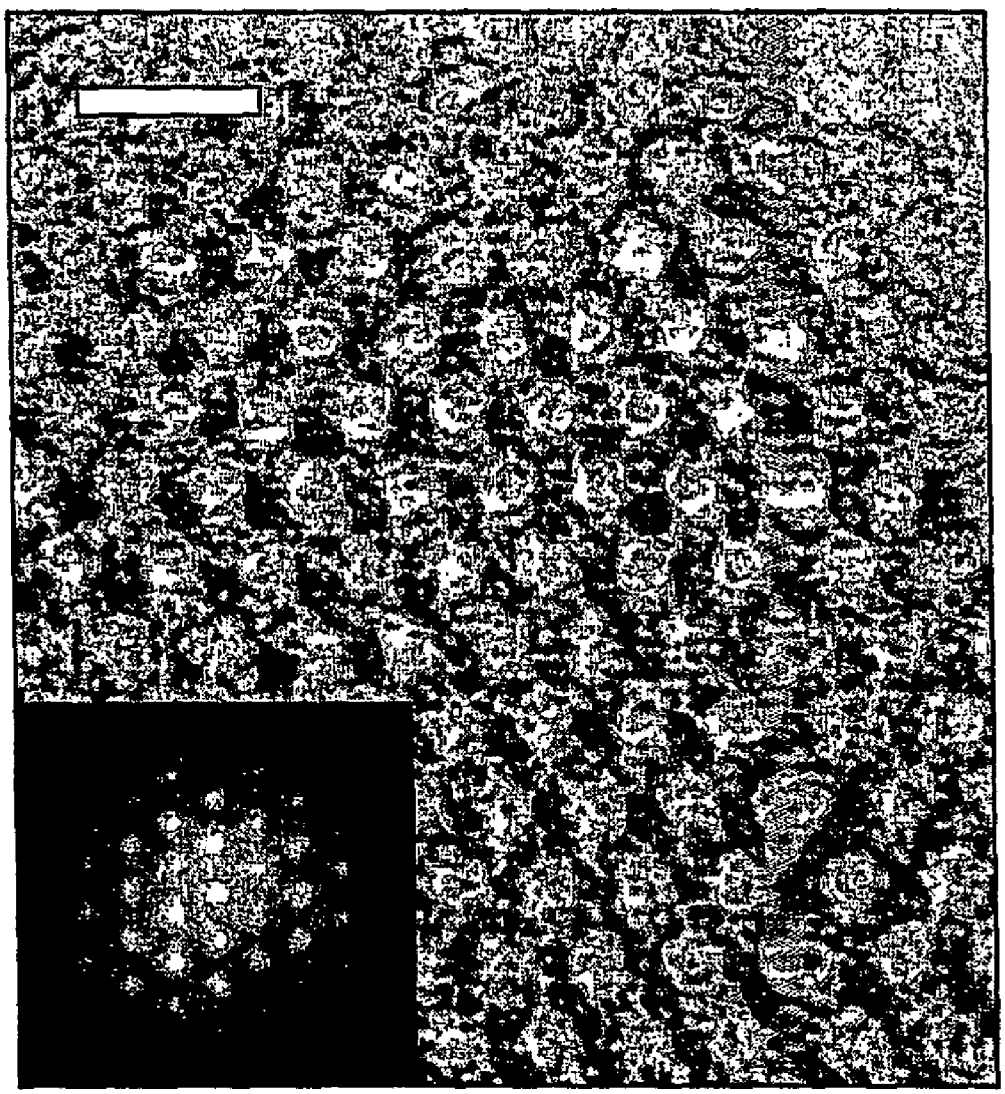
FIG. 3 shows a HREM image, together with electron diffraction pattern insert (insert for the Fourier transform at bottom left) of a mesoporous silica material according to another embodiment of the invention named Zeotile-4 (scale bar represents 20 nm).

High-resolution electron microscopy (HREM) was used to characterise the structural order of the material obtained, herein named as Zeotile-4. As shown in FIG. 3, Zeotile-4 is made up from stapled large nanoslabs arranged in a hexagonal appearing tile, the large nanoslabs used as building units being clearly visible in the image. In HREM, the tiling patterns show a high perfection throughout the individual Zeotile particles reaching micrometer sizes. The Fourier transform of the HREM image (insert at bottom left of the figure) only shows information on the nanoslab tiling; no reflections related to the internal nanoslab structure were detected.

The integrity of the Silicalite-1 building blocks in this material was also confirmed with $^{29}$Si MAS NMR (nuclear magnetic resonance), showing the unique silicon connectivity of the nanoslabs to be maintained during the tiling process and templating organic species evacuation. In addition, nitrogen adsorption isotherms at −196° C. and alkane separation experiments confirmed the presence of Silicalite-1 microporosity next to mesopores with precise diameters (9.4 nm for example 2).

Example 3

6 g of cetyltri-methylammonium bromide (commercially available from Acros, 99% purity) in powder was slowly added to 20 g of the nanoslab suspension prepared according to example 1 under vigorous stirring, followed by addition of 60 g water. The slurry was stirred for 24 hours and subsequently heated at 100° C. for 72 hours under quiescent conditions. The resulting precipitate was then treated by the same method as in example 1.

Figure 2:
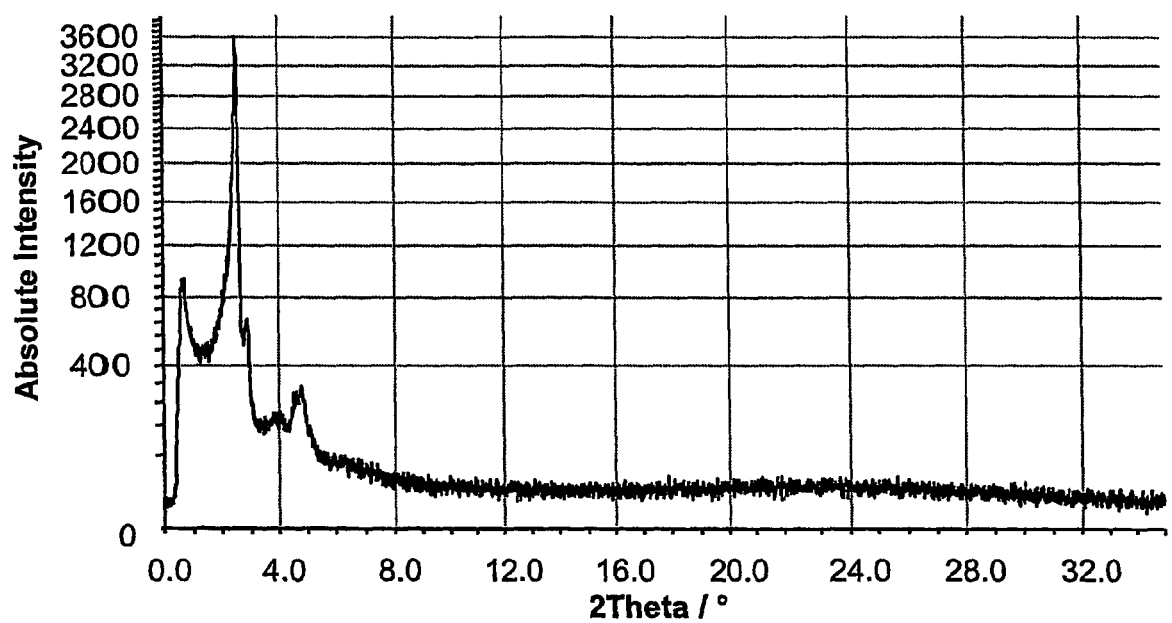
FIG. 2 shows the X-ray diffraction pattern, at diffraction angles $\Theta$ from 0 to 16 degrees (2$\Theta$ from 0 to 32 deg.) of a mesoporous silica material according to another embodiment of the invention named Zeotile-2.

Powder X-ray diffraction (XRD), shown in FIG. 2, and high-resolution electron microscopy (HREM) were used to characterise the structural order of the material obtained, named Zeotile 2. As shown in FIG. 2, the XRD spectrum did not reveal internal nanoslab information but only information related to the tiling pattern of said nanoslabs, all characteristic peaks being located at angles θ below 3 degrees (2θ below 6 degrees). Individual dispersed nanoslabs, presumably because of their small size, did not give rise to Bragg type diffraction related to their internal structure.

Electron diffraction (ED) and HREM images demonstrated that Zeotile-2 is built from very similar units as Zeotile-1 (example 1), but has body centered cubic symmetry.

Example 4

The release of itraconazole (purity above 99%) from Janssen Pharmaceutica (Beerse, Belgium) was investigated with solid dispersions from various zeolitic materials. After complete dissolution of itraconazole in methylene chloride, SBA-15 (a material made in accordance with U.S. Pat. No. 6,592,764) or MCM-41 (a commercially available zeolite) were suspended and the mixture was stirred for 20 hours. Subsequently, the solvent is removed by rota-evaporation or spray-drying and the powder was further dried for 48 hours at 40° C. under reduced pressure. In this way solid dispersions having a drug loading of 20% by weight were prepared. In order to study the release of the drug substance, the solid dispersions were suspended in simulated gastric fluid (defined according to U.S. Pharmacopeia XXV) at 37° C. under stirring. At specific time intervals, the concentration of the drug substance in the dissolution medium was measured using high performance liquid chromatography (HPLC). All experiments were performed in triplicate.

Concentrations of itraconazole were determined using an isocratic HPLC method. The HPLC system consisted of a Lachrom® L-7100 HPLC pump, an autosampler model L-7200 equipped with a 100 µl loop, a UV detector model L-7420 set at 257 nm, and an Interface D-7000, all from Merck (Darmstadt, Germany). UV signals were monitored and peaks were integrated using the D-7000 HSM software. All chromatographic separations were performed at room temperature. The 12.5×0.4 cm column was packed with LiChrospher® 100 RP-18 (5 µm) (also from Merck, Darmstadt, Germany). The mobile phase consisting of acetonitrile/tetrabutylammonium hydrogenosulfate 0.01N (55:45 volume/volume), was filtered through a membrane filter (0.45 µm) and degassed by ultrasonication before use. The flow rate amounted to 1 ml/minute.

Figure 4:
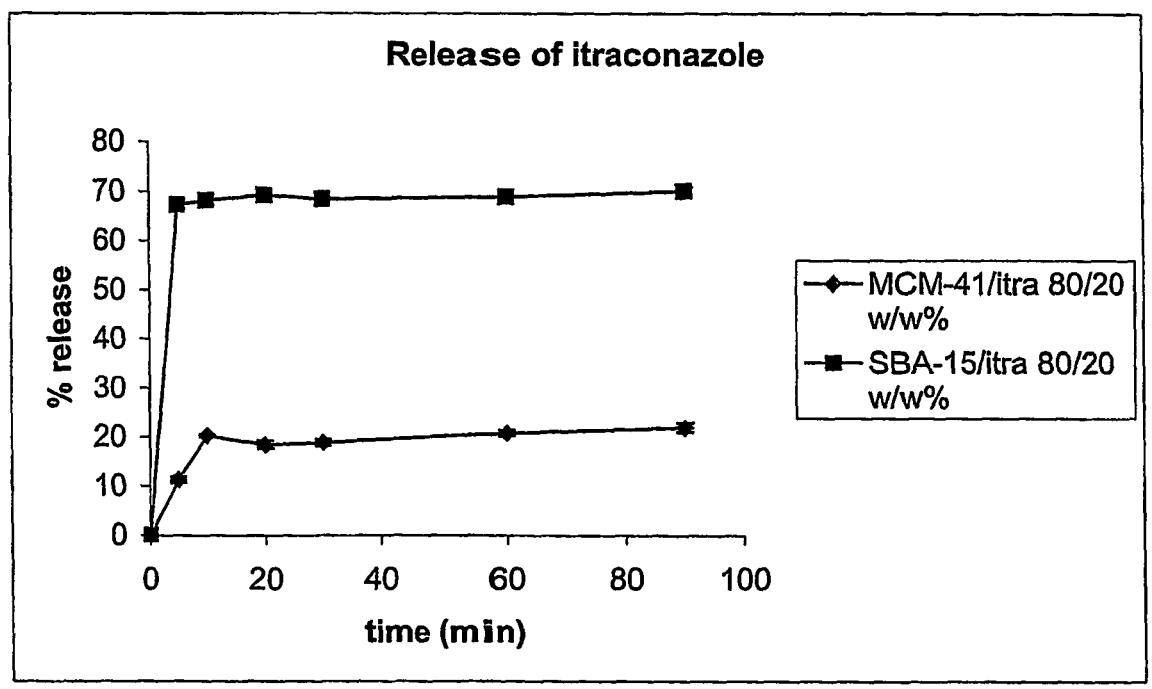
FIG. 4 shows the release of itraconazole in simulated gastric fluid from solid dispersions made up of 20% by weight of itraconazole and 80% by weight of a mesoporous silica material known under the reference SBA-15 (upper curve) or a zeolite known as MCM-41 (lower curve).

FIG. 4 shows the dissolution of itraconazole in simulated gastric fluid from solid dispersions made up of 20% of drug and 80% of either SBA-15 or MCM-41. In the case of SBA-15, the rate of release (about 68% after 10 minutes) as well as the maximal amount of drug dissolved is significantly higher than in the case of MCM-41.

Example 5

Figure 5:
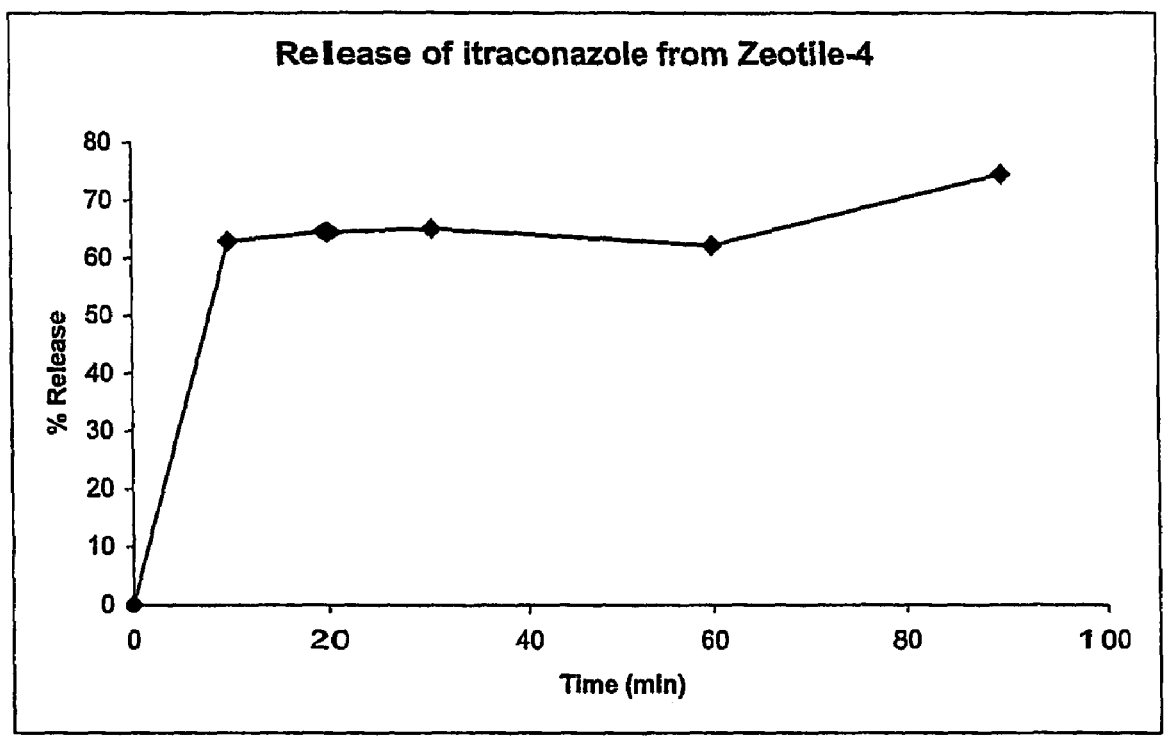
FIG. 5 shows the release of itraconazole in simulated gastric fluid from solid dispersions made up of 20% by weight of itraconazole and 80% by weight of a mesoporous silica material according to an embodiment of the invention named Zeotile-4.

The procedure of example 4 was repeated, except that the zeolitic material used was that of example 3, i.e. Zeotile-4. FIG. 5 shows the dissolution of itraconazole in simulated gastric fluid from solid dispersions made up of 20% of drug and 80% of Zeotile-4. From a steady comparison with FIG. 4, it is clear that the rate or release in the case of Zeotile-4 (about 63% release after 10 minutes) is significantly higher than in the case of MCM-41 (about 20% after 10 minutes).

Example 6

Figure 6:
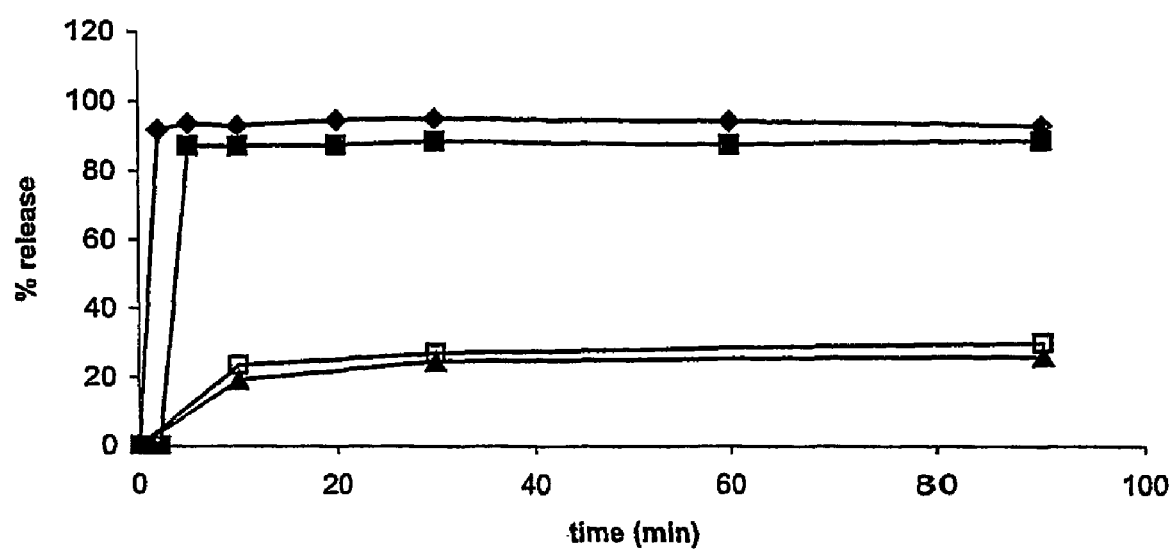
FIG. 6 shows the release of diazepam from solid dispersions made up of 30% by weight of diazepam and 70% by weight of a mesoporous silica material according to an embodiment of the invention named Zeotile-4.

The procedure of example 5 was repeated, except that the drug used was diazepam. FIG. 6 shows the dissolution of diazepam in simulated gastric fluid from the following solid dispersions:
30% drug loading and 4% Mirj (♦);
30% drug loading (■);
physical mixture containing 30% drug (not treated) (♦);
physical mixture containing 30% drug (treated) (□).

The invention claimed is:

1. A crystalline mesoporous silica material being obtained by assembly of nanometer size building units having zeolite framework, said crystalline mesoporous silica material having two or more levels of porosity and structural order, wherein the internal structure of said nanometer size building units does not give rise to Bragg type diffraction in a powder X-ray diffraction pattern of said crystalline mesoporous silica material, wherein said nanometer size building units are nanoslabs of substantially uniform size having the Silicalite-1 zeolite framework, and wherein said two or more levels of porosity comprise at least a microporosity inside said nanoslabs and at least a mesoporosity between said nanoslabs.

2. A crystalline mesoporous silica material according to claim 1, wherein said nanoslabs are generated by tetrapropylammonium-ion mediation.

3. A crystalline mesoporous silica material according to claim 1, wherein said nanoslabs are linked through their corners, edges or faces following patterns imposed by interaction with a cationic surfactant or triblock copolymer molecule.

4. A crystalline mesoporous silica material according to claim 1, wherein said absence of Bragg type diffraction from nanometer size building units manifests itself by the absence of peaks in a powder X-ray diffraction pattern at interplanar spacings below about 1.5 nm.

5. A process for making a crystalline mesoporous silica material, said crystalline mesoporous silica material being obtained by assembly of nanometer size building units having zeolite framework, said crystalline mesoporous silica material having two or more levels of porosity and structural order, wherein said building units are nanoslabs of substantially uniform size having the Silicalite-1 zeolite framework, comprising the steps of (a) generating said nanoslabs having said zeolite framework by tetrapropylammonium-ion mediation and (b) assembling said nanoslabs through interaction with a cationic surfactant or triblock copolymer molecule, wherein said two or more levels of porosity comprise at least a microporosity inside said nanoslabs and at least a mesoporosity between said nanoslabs.

6. A process according to claim 5, further comprising the step of removing said tetrapropylammonium-ion and said cationic surfactant or triblock copolymer molecule.

7. A process according to claim 6, further comprising the step of obtaining a powder X-ray diffraction spectrum on said crystalline mesoporous silica material, wherein the internal structure of said nanometer size building units does not give rise to Bragg type diffraction in said powder X-ray diffraction pattern of said crystalline mesoporous silica material.

8. A process for making a substantially crystalline mesoporous oxide based material being obtained by assembly of nanometer size building units having zeolite framework, wherein said assembly proceeds in the presence of one or more amphiphilic non-anionic surfactants, wherein said substantially crystalline mesoporous oxide based material has two or more levels of porosity and structural order, and wherein the internal structure of said nanometer size building units does not give rise to Bragg type diffraction in a powder X-ray diffraction pattern of said substantially crystalline mesoporous oxide based material, comprising the steps of (a) generating said nanometer size building units having zeolite framework by means of a mediating agent selected from the group consisting of tetraalkylammonium ions, tetraalkylphosphonium ions or gemini (dimeric) tetraalkylammonium ions wherein the alkyl group has from 2 to 4 carbon atoms, and (b) assembling said nanometer size building units through interaction with said one or more amphiphilic non-anionic substances to yield a mesoporous oxide based material, wherein said nanometer size building units are nanoslabs of substantially uniform size having the Silicalite-1 zeolite framework and wherein said two or more levels of porosity comprise at least a microporosity inside said nanoslabs and at least a mesoporosity between said nanoslabs.

9. A pharmaceutical composition comprising a biologically active species and a substantially ordered mesoporous oxide based material, wherein said ordered oxide based material is a crystalline mesoporous silica material being obtained by assembly of nanometer size building units having zeolite framework, said crystalline mesoporous silica material having two or more levels of porosity and structural order, and wherein the internal structure of said nanometer size building units does not give rise to Bragg type diffraction in a powder X-ray diffraction pattern of said crystalline mesoporous silica material and said nanometer size building units are nanoslabs of substantially uniform size having the Silicalite-1 zeolite framework and wherein said two or more levels of porosity comprise at least a microporosity inside said nanoslabs and at least a mesoporosity between said nanoslabs.

10. A crystalline mesoporous silica material comprising nanometer size building units, wherein said crystalline mesoporous silica material has two or more levels of porosity and structural order, wherein the internal structure of said nanometer size building units does not give rise to Bragg type diffraction in a powder X-ray diffraction pattern of said crystalline mesoporous silica material, wherein said nanometer size building units are nanoslabs of substantially uniform size having the Silicalite-1 zeolite framework, and wherein said two or more levels of porosity comprise at least a microporosity inside said nanoslabs and at least a mesoporosity between said nanoslabs.

11. A crystalline mesoporous silica material according to claim 10, wherein said nanoslabs are linked through their corners, edges or faces following patterns imposed by interaction with a cationic surfactant or triblock copolymer molecule.

12. A crystalline mesoporous silica material according to claim 10, wherein said absence of Bragg type diffraction from nanometer size building units manifests itself by the absence of peaks in a powder X-ray diffraction pattern at interplanar spacings below about 1.5 nm.

* * * * *